United States Patent [19]

Dice et al.

[11] Patent Number: 4,934,450
[45] Date of Patent: Jun. 19, 1990

[54] DEVICE FOR COLLECTING OIL SAMPLES

[76] Inventors: Michael J. Dice, Box 474; Cary A. Hay, Box 2032, both of Kindersley, Saskatchewan, Canada, S0L 1S0

[21] Appl. No.: 345,829

[22] Filed: May 1, 1989

[51] Int. Cl.$^5$ ............................................. E21B 43/00
[52] U.S. Cl. ..................................... 166/75.1; 166/265; 55/337
[58] Field of Search .................... 166/75.1, 162, 264; 175/59; 73/153, 155, 863.23; 55/337

[56] References Cited

U.S. PATENT DOCUMENTS

| | | | |
|---|---|---|---|
| 4,402,715 | 9/1983 | Ruyak et al. | 55/337 X |
| 4,668,252 | 5/1987 | Gerdau | 55/337 X |
| 4,668,256 | 5/1987 | Billiet et al. | 55/337 X |

FOREIGN PATENT DOCUMENTS 1139127 1/1983 Canada.

*Primary Examiner*—William P. Neuder
*Attorney, Agent, or Firm*—George Haining Dunsmuir

[57] ABSTRACT

A simple device for collecting an oil sample from a well in a clean manner includes a generally cylindrical casing, an inlet tube connected at one end to a wellhead and at the other end to the casing near the top end for introducing an oil sample into the casing tangentially, so that heavy oil is forced outwardly against the interior of the casing and flows downwardly to the bottom thereof, a valved bottom inlet in the casing for discharging oil therefrom to a sample bottle, and a top outlet with a steel wood filter therein for discharging gas separating from the oil through the top wall of the casing.

5 Claims, 2 Drawing Sheets

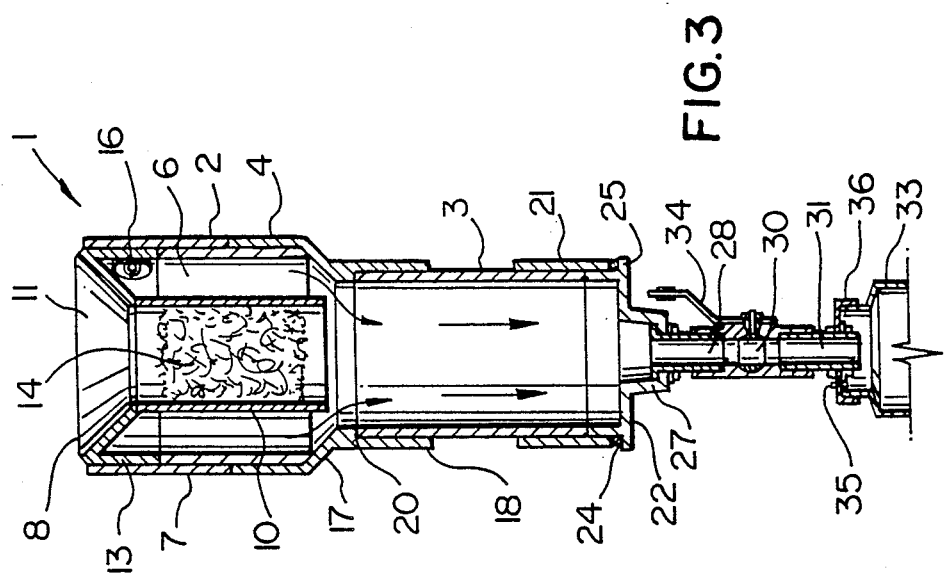
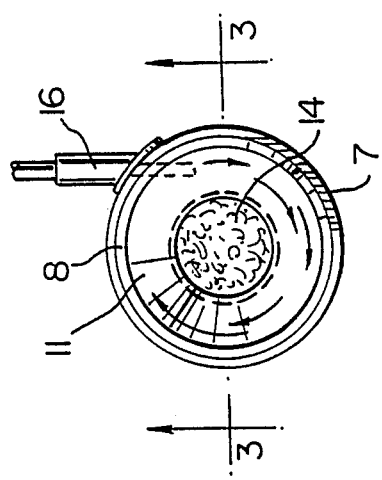
FIG. 3
FIG. 2

DEVICE FOR COLLECTING OIL SAMPLES

BACKGROUND OF THE INVENTION

This invention relates to a device for collecting a fluid sample from a well, and in particular to a device for collecting a fluid sample from a well, and in particular to a device for collecting an oil sample at a wellhead.

In the oil industry, it is frequently necessary to obtain oil samples from producing wells, such samples may be required as often as weekly. The obtaining of oil samples has always been a messy and bothersome task. The inventors are aware of no commercially available product which will make the sampling job easier and less messy.

The problems involved in the collecting of fluid samples from wells are discussed at length in the preamble portion of Canadian Patent No. 1,139,127, which issued to G. J. Boyle et al on Jan. 11, 1983. The solution to such problems offered by the Boyle et al patent includes a pipe containing a body with a plurality of passages therein for mixing the components of the well fluid, and a sample tube extending into the pipe downstream of the mixing body for removing a fluid sample. It is readily apparent that the Boyle et al invention is designed to remove a more or less completely mixed well sample, i.e. a sample containing gas and liquid for analysis. Boyle et al offers no solution to the problem of separating gas and liquid at the wellhead and collecting the remaining liquid.

The object of the present invention is to provide a solution to the above problem in the form of a relatively simple device for collecting a sample at a wellhead, and for separating at least some gas from the sample.

BRIEF SUMMARY OF THE INVENTION

Accordingly, the present invention relates to a device for collecting an oil sample from a well comprising cylindrical casing means; inlet means proximate the top end of said casing means for introducing a well sample tangentially into said casing means; whereby heavier oil is forced against the interior of the casing means and flows downwardly to the bottom thereof; first outlet means in the bottom end of said casing means for discharging oil therefrom; second outlet means in the top of said casing means for discharging gas from said device.

BRIEF DESCRIPTION OF THE DRAWINGS

The invention will be described in greater detail with reference to the accompanying drawings, which illustrates a preferred embodiment of the invention, and wherein:

FIG. 2 is a plan view of the device of FIG. 1; and

FIG. 3 is a cross section taken generally along line III—III of FIG. 2.

DESCRIPTION OF THE PREFERRED EMBODIMENT(S)

Figure 1:
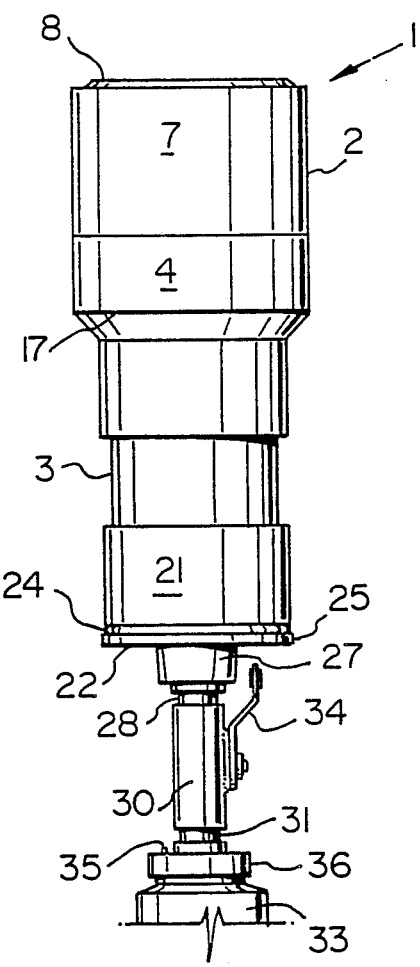
FIG. 1 is a side elevational view of a sample collecting device in accordance with the present invention.

Referring to the drawing, the device of the present invention includes an elongated, basically cylindrical casing generally indicated at 1. The casing 1 is defined by an upper tubular section 2, a lower tubular section 3 and an adapter 4 for connecting the smaller diameter lower section 3 to the upper section 2. The upper section 2 is defined by a tubular inner wall 6 surrounded at the bottom end by the adapter 4 and at the top end by a sleeve 7. The inner wall 6 supports a filter element 8 defined by a tubular central body 10 and an inverted frusto-conical cover 11 which includes an outer ring 13 for mounting the element 8 in the sleeve 7 on the top end of the wall 6. The body 10, which extends downwardly beyond the bottom end of the upper casing section 2, contains a steel wool gas scrubber or filter 14. An inlet tube 16 for carrying a well sample from a wellhead (not shown) extends tangentially into the upper section 2 of the casing 1 near the top end thereof.

The adapter 4 includes an inverted frusto-conical centre section 17 and a reduced diameter bottom end 18 for receiving the casing section 3. An internal shoulder 20 is provided in such bottom end 18 for limiting movement of the lower casing section 2 into the adapter.

A sleeve 21 surrounds and extends downwardly from the bottom end of the lower casing section 3 for receiving the bottom end 2 of the casing. An O-ring 24 is provided between the sleeve 21 and a flange 25 on the bottom end 22 of the casing. A well 27 in the bottom end 22 of the casing supports an outlet duct 28, which carries liquid from the casing through a ball valve 30 and a tube 31 to a sample bottle 33. A handle 34 is provided on the valve 30 for opening and closing the latter.

In use, the tube 16 is connected to the wellhead at the location normally occupied by the pressure gauge (not shown) using a hydraulic fitting. With the valve 30 open, when the wellhead valve is opened, gas and oil enter the casing 1 through the tube 16. Because the gas and oil enter the casing 1 tangentially, heavier oil is forced outwardly, and fed by gravity to the bottom of the casing 1 for discharge through the valve 30 to the sample bottle 33. An air bleed tube 35 (FIG. 3) is provided in the top end 36 of the sample bottle 33, so that oil can readily flow into the bottle. Gas passes into the bottom end of the filter body 10 and is discharged through the steel wool filter 14.

Thus, it is seen that the device acts as a centrifugal separator, whereby an oil sample substantially free of gas is discharged from the bottom end of the casing 1 to the sample bottle 33.

What we claim is:

1. A device for collecting an oil sample from a well comprising cylindrical casing means, said casing means including an upper inlet section, a lower oil outlet section of smaller diameter than said inlet section and inverted frusto-conical adapter means interconnecting said inlet and outlet sections for ensuring the smooth flow of liquid therebetween; inlet means on one side of the top end of said casing means for introducing a well sample tangentially into said casing means, whereby heavier oil is forced against the interior of the casing means and flows downwardly to the bottom thereof; first outlet means in the bottom end of said casing means for discharging oil therefrom; and second outlet means in the top for discharging gas from the device, said second outlet means including tube means extending into the top end of said casing means, said tube means being co-axial with and smaller in diameter than said casing means, and extending downwardly beyond said inlet means into said adapter means to define an annular oil receiving passage with said adapter means.

2. A device according to claim 1, including outlet tube means connected to said first outlet means; valve means in said outlet tube means for controlling the flow of liquid from said casing means; and cover means connected to the bottom end of said outlet tube means for defining the top end of a sample bottle to ensure the smooth flow of oil into the bottle.

3. A device according to claim 2, including air bleed means in said cover means for ensuring that oil readily flows into the sample bottle.

4. A device according to claim 1, wherein said tube means is substantially the same length as the inlet section of said casing means.

5. A device according to claim 1 including valve means in said first outlet means for controlling the flow of liquid from said casing means.

* * * * *